US008049039B2

(12) United States Patent
Nguyen et al.

(10) Patent No.: US 8,049,039 B2
(45) Date of Patent: Nov. 1, 2011

(54) PROCESS FOR PREPARATION OF ALKOXYLATED ALKYLAMINES/ALKYL ETHER AMINES WITH PEAKED DISTRIBUTION

(75) Inventors: Giao Vinh Nguyen, Friendswood, TX (US); James Alfred Ragains, Fort Worth, TX (US); Kha Carl Dang Nguyen, Seabrook, TX (US); Charles Woodville Davis, Houston, TX (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 12/305,082

(22) PCT Filed: Jun. 21, 2007

(86) PCT No.: PCT/EP2007/056178
§ 371 (c)(1),
(2), (4) Date: Dec. 16, 2008

(87) PCT Pub. No.: WO2007/147866
PCT Pub. Date: Dec. 27, 2007

(65) Prior Publication Data
US 2009/0209788 A1    Aug. 20, 2009

Related U.S. Application Data

(60) Provisional application No. 60/816,196, filed on Jun. 23, 2006.

(51) Int. Cl.
*C07C 213/04* (2006.01)
(52) U.S. Cl. .................................. 564/475; 564/477
(58) Field of Classification Search .................. None
See application file for complete search history.

(56) References Cited

FOREIGN PATENT DOCUMENTS
EP        0 339 426 A2    11/1989
WO     WO 2006/034459 A1    3/2006

OTHER PUBLICATIONS

International Search Report for International Application No. PCT/EP2007/056178; Completion Date Sep. 13, 2007.
English Translation of Abstract of EP033426, (1989).

*Primary Examiner* — Brian J Davis
(74) *Attorney, Agent, or Firm* — Ralph J. Mancini (57) ABSTRACT

The present invention generally relates to a process for preparing alkoxylated alkylamines and/or alkyl ether amines. The process consists of two stages and utilizes a catalyst with a multiple-charge counterion. The alkoxylated alkylamines and alkoxylated alkyl ether amines prepared by the process possess the peaked ethoxylation distribution and contain less hazardous by-product.

27 Claims, 5 Drawing Sheets

Figure 1

Homolog distribution of tallow amine prepared with 5 moles of ethylene oxide by the regular hydroxide-catalyzed process Structure of hydrotalcite/hydrotalcite-like compounds

Homolog distribution of the 5-mole EO adduct of coco amine prepared by the regular ethoxylation process (T15R) and the new ethoxylation process (T15-Ba). The degree of peaking is 57.3 for T15R and 71.9 for T15-Ba.

Figure 4

Homolog distribution of 10-mole EO adduct of coco amine prepared by the regular ethoxylation process (T20R) and the new ethoxylation process (T20-Sr). The degree of peaking is 42.8 for T20R and 50.8 for T20-Sr.

Figure 5

Homolog distribution of 5-mole EO adduct of tallow amine prepared by the regular ethoxylation process (T15R) and the new ethoxylation process (T15-HTC). The degree of peaking is 57.3 for T15R and 75.9 for T15-HTC.

PROCESS FOR PREPARATION OF ALKOXYLATED ALKYLAMINES/ALKYL ETHER AMINES WITH PEAKED DISTRIBUTION

FIELD OF THE INVENTION

The present invention relates to a process for the preparation of alkoxylated alkylamines or alkoxylated alkyl ether amines with peaked distribution using ionic catalysts having multiple-charge counterions.

BACKGROUND OF THE INVENTION

Alkoxylated alkylamines and alkyl ether amines, particularly ethoxylated alkyl-amines and ethoxylated alkyl ether amines, have many applications in industry. They can be usefully employed as adjuvants in cleaning formulations, textile processing aids, dye transfer inhibitors, acid thickeners, detergent boosters, degreasers, anti-static agents, and the like.

Alkoxylated alkylamines and alkoxylated alkyl ether amines are materials possessing the following general structure (I):

wherein R is selected from a linear or branched, saturated or non-saturated alkyl group containing 8-22 carbon atoms or a group of the formula:

$$R-O-(A)_a-(B)_b-(C)_c,$$

wherein A and B are alkylene oxide groups containing 2-4 carbon atoms, C is an alkylene group containing 3-4 carbon atoms, a, b each vary from 0-5, c is 1, X, Y, Z are alkylene oxide groups containing 2-4 carbon atoms, x is 1, and y varies from 1-15.

As illustrated by general formula (I), the alkoxylated alkylamines/alkoxylated alkyl ether amines possess a surfactant structure which is composed of the lipophilic groups (R) and the hydrophilic groups (polyalkylene oxide). In their designed applications, the performance of alkoxylated alkylamines and alkoxylated alkyl ether amines is dependent on a balance between the lipophilicity and the hydrophilicity provided by these groups.

Even when the lipophilicity-hydrophilicity balance does exist, the performance of the alkoxylated alkylamines/alkoxylated alkyl ether amines is not necessarily optimal. Traditionally, these materials are prepared from the base-catalyzed alkoxylation of the corresponding alkylamines/alkyl ether amines. Such an alkoxylation reaction is actually the polymerization reaction of alkylene oxide, including the characteristic propagation and chain transfer steps of the polymerization process. For this reason, the resulting alkoxylated alkylaminelalkyl ether amine is not a pure compound, but a mixture of many homologs.

Figure 1:
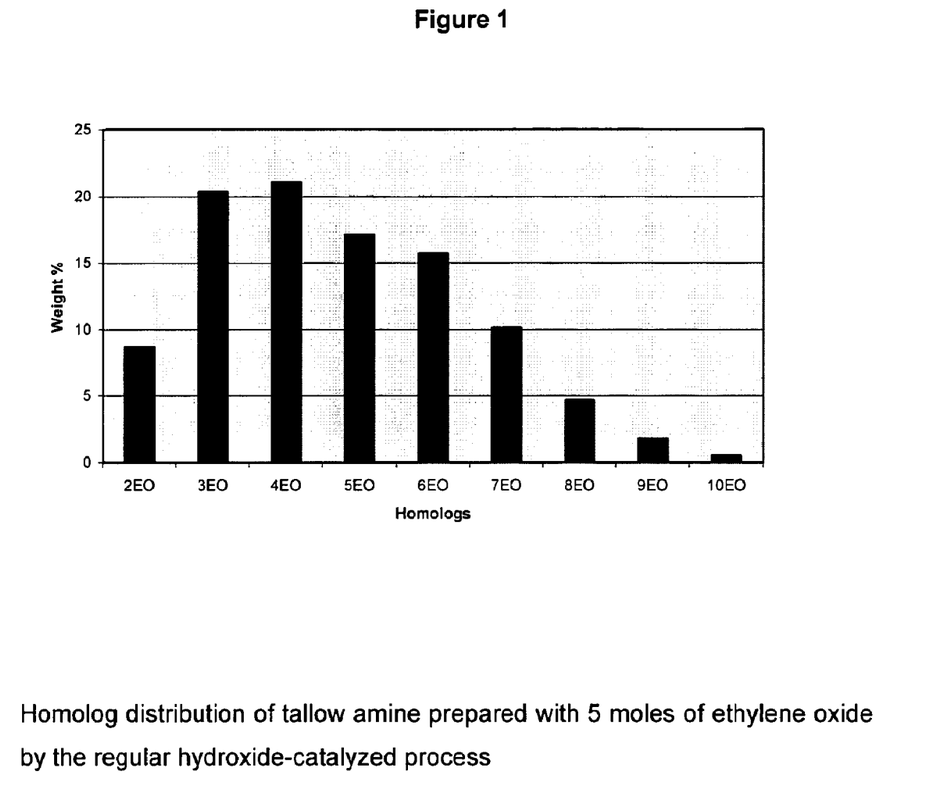
FIG. 1 shows the homolog distribution of tallow amine prepared with 5 moles of ethylene oxide by the regular hydroxide-catalyzed process.

As an example, FIG. 1 illustrates the homolog distribution of ethoxylated tallow amine prepared from the regular (hydroxide-catalyzed) ethoxylation of tallow amine with 5 moles of ethylene oxide. As shown in FIG. 1, the resulting ethoxylated product is not a single compound containing five ($CH_2CH_2O$) units as the general structure (structure I, with 2x+2y=5) may suggest. Instead, the product is a mixture of several homologs whose total of ethylene oxide units varies from 2 to 10. Among these homologs, only those in the middle of the distribution range (3EO-5EO) have the proper lipophilic-hydrophilic balance and, therefore, are preferred. Homologs with a shorter EO chain length (<3EO) or a longer EO chain length (>5EO) are not desirable, since they are either too lipophilic or too hydrophilic for the applications utilizing this product. Therefore, it is advantageous to develop an alkoxylation process that results in alkoxylated products with peaked distribution.

As covered in the prior art, an ethoxylation process offering peaked distribution has been developed; the ethoxylated alkylamines/alkyl ether amines having peaked distribution were successfully prepared by ethoxylation of the starting alkylamine catalyzed by a Lewis acid. However, hazardous property of the catalyst, lower reaction rate, degradation of the product colour, and formation of by-products have seriously limited the utilization and usefulness of this acid-catalyzed ethoxylation process and adversely affect the properties and the attractiveness of the ethoxylated products.

Accordingly, it is an object of the present invention to develop a process for the preparation of alkoxylated ethoxylated alkylamines and alkyl ether amines, particularly ethoxylated alkylamine and ethoxylated alkyl ether amine with peaked distribution having greatly minimized drawbacks compared to those associated with the acid-catalyzed process.

SUMMARY OF THE INVENTION

The present invention generally relates to an alkoxylation process for the preparation of alkoxylated alkylamines/alkoxylated alkyl ether amines with peaked distribution and to the products prepared therefrom. The specific process of the invention utilizes a catalyst having a multiple-charge counterion to promote the peaked distribution of the resulting alkoxylated products.

DETAILED DESCRIPTION OF THE DRAWINGS

DETAILED DESCRIPTION OF THE INVENTION

The alkoxylated alkylamines and ethoxylated alkyl ether amines of the invention are materials possessing the following general structure (I):

wherein R is selected from a linear or branched, saturated or non-saturated alkyl group containing 8-22 carbon atoms or a group of the formula wherein A and B are alkylene oxide groups containing 2-4 carbon atoms, C is an alkylene group containing 3-4 carbon atoms, a, b each vary from 0-5, c is 1, X, Y, Z are alkylene oxide groups containing 2-4 carbon atoms, x is 1, and y varies from 1-15.

The alkoxylated alkylamineslalkyl ether amines of the invention are not single compounds as suggested by their general structure (I), but rather, they are components in a mixture of several homologs of varied polyalkylene oxide chain length. Among the homologs, only those with the number of total alkylene oxide units closer to the most abundant alkylene oxide adduct are preferred; homologs whose number of total alkylene oxide units is much lower or much higher than the most abundant alkylene oxide adduct are undesirable, since they are too liphophilic or too hydrophilic to be suitable for the applications for which the alkoxylated alkylamines/alkyl ether amines are designed.

Alkoxylated alkylamines and alkoxylated alkyl ether amines are prepared from the reaction of the corresponding primary alkylamines/alkyl ether amines with a selected number of moles of alkylene oxide. Using ethoxylated alkylamines (IA) as an example, the prior art generally describes the synthesis of ethoxylated alkylamines in a two-stage process:

1) Reaction of two moles of ethylene oxide with the primary alkylamine (II) to yield the intermediate (III) (N,N-bis-(2-hydroxyethyl)N-alkylamine). No catalyst is required for this reaction.

2) Reaction of additional moles of ethylene oxide with the intermediate (III) to yield the desired final ethoxylated alkylamine product (V) not having a peaked distribution. This reaction requires the use of a catalyst.

Based on the catalyst type, two types of ethoxylation processes are covered in the prior art. In the regular ethoxylation process, the catalyst is a base, preferably a hydroxide such as sodium hydroxide or potassium hydroxide. In the process of the prior art that produced alkoxylate products with peaked distribution, the catalyst is a Lewis Acid catalyst such as boron trifluoride.

In the process utilizing a base catalyst, the ethoxylation in the second stage is actually the polymerization of the s moles of ethylene oxide and follows the mechanism of a polymerization reaction. The base catalyst, sodium hydroxide or potassium hydroxide for example does not actually catalyze the reaction. Instead, the catalyst reacts with the intermediate (III) to form an alkoxide that, in turn, initiates the polymerization. As with the ethoxylation of alcohol, whose mechanism has been fully established, the polymerization of ethylene oxide in Stage 2 also consists of the other characteristic steps of a polymerization reaction: the propagation step which results in a flat distribution, and the termination, or chain transfer, step which promotes the peaked distribution.

The base-catalyzed ethoxylation process is typically preferred for its high reaction rate, low formation of undesired by-products, and lighter colour of the resulting ethoxylated product. However, it also inherits a property that is associated with the polymerization reaction: the final ethoxylated alkyl (ether) amine ethoxylate (I) has a wide and flat ethoxylation distribution and possesses a higher concentration of the undesired (too lipophilic/too hydrophilic) homologs.

The second ethoxylation process of the prior art was designed to obtain the preferred peaked distribution. In this process, the ethoxylation is catalyzed by a Lewis acid such as boron triflouride and follows a different mechanism. The resulting ethoxylated product possesses the peaked distribution, with the highest concentration of the homologs in the middle of the distribution range. Because the concentration of the undesired homologs is lower in this case, the performance of the ethoxylated alkylamines/alkyl ether amines in the applications they are designed for is optimized.

Whereas the acid-catalyzed process promotes the peaked ethoxylation distribution and thus enhances the performance of the resulting ethoxylated alkylamine/alkyl ether amine, there are several drawbacks, including but not limited to the following restrictions of its utilization and usefulness.

The catalyst (boron trifluoride) is not only expensive, but also a hazardous material. The use of this catalyzed material requires elaborate equipment for its storage and charging to the reactor.

The process also enhances the formation of undesired by-products, most noticeably dioxane and ethylene glycol derivatives (EGDs). Depending on the number of moles of ethylene oxide used in the ethoxylation process, the dioxane content in the ethoxylated products could be as high as 25 000 ppm. Dioxane is perceived as a hazardous material and it is desirable for it to be removed or minimized in the ethoxylated product. Removal of such a high concentration of dioxane requires additional equipment, greatly prolongs the cycle time, and reduces the product yield. The EGD content in the products (up to 10%) is much higher than that of dioxane. While it is not a hazardous material, the high content of EGDs lowers the concentration of the desired ethoxylated alkylamine and thus adversely affects the performance or effectiveness of the ethoxylated product in its application.

The colour of the resulting ethoxylated product degrades over time.

The process does not work with propylene oxide.

The process of the present invention possesses the advantages of the above-described base-catalyzed and acid-catalyzed processes while eliminating or greatly reducing the drawbacks inherent in same. Specifically, the present process enables the preparation of alkoxylated alkylamines/alkyl ether amines with the desired peaked alkoxylation distribution, thus ensuring optimum performance in their respective applications. Simultaneously, the problem associated with the use of the acid catalyst, including the high cost and hazardous property of the catalyst, the formation of hazardous, undesired by-products, the prolonged cycle time, and the colour degradation, are eliminated.

In accordance with the invention, the present inventors discovered that to be able to produce the peaked distribution for the alkoxylated alkyl (ether) amine, a catalyst promoting the termination (chain transfer) step of the polymerization process must be used to initiate the polymerization of the alkylene oxide used in the second alkoxylation stage. The inventors also discovered that such a catalyst could be drawn from selected groups of organic, inorganic, and organometallic materials that share a common property: they all are ionic compounds having multiple-charge counterions.

As discovered in this invention, one of the selected catalyst groups is derived from the binary compounds of the Group II element, each composed of two single charge anions and a counterion bearing two positive charges.

The preferred Group II elements include those with low first ionization potential, and particularly with low second ionization potential. Strontium and barium are examples of Group II elements that work particularly well. Radium also has low first and second ionization potentials; however, it is not preferred due to its radioactive property. Other Group II elements, including beryllium, magnesium, and calcium may not be effective, since their higher ionization potentials make the formation of multiple-charge counterions more difficult. Strontium hydroxide and barium hydroxide are the preferred catalysts, though other binary compounds of strontium and barium, including but not limited to acetate, carboxylate, chloride can also be used. It is important to note that the reaction between the tertiary amine (III) and the catalysts of this selected group to form the initiator for the polymerization of alkylene oxide is reversible. Therefore, to maximize the alkoxylation reaction in Stage 2 of the process and to minimize the formation of the undesired alkoxylated by-product, the by-product formed from the reaction between the catalyst and the tertiary amine (III) (water if strontium/barium hydroxide is used) must be removed from the reaction mixture as soon as it is formed.

Compounds of elements of Group III, particularly aluminium, gallium, and indium, and of transition metal, particularly manganese, iron, copper, chromium, nickel, cobalt, and lanthanum, are capable of having counterions with multiple ionic (positive) charges. However, like compounds of magnesium and beryllium, due to the high second ionization potential of the elements, these materials are not effective as catalysts for the preparation of alkoxylated alkyl/alkyl ether amines with peaked distribution. However, as discovered in this invention, selected ionic complex materials containing these elements are suitable as catalysts for the alkoxylation process described in this invention.

Hydrotalcite and hydrotalcite-like compounds are one group of these selected ionic complex materials. Their chemical composition can be expressed by the formula $M^{II}_{1-x}M^{III}_x(OH)_2 A^{n-}_{x/n} \cdot mH_2O$, wherein $M^{II}$ is a divalent cation such as $Mg^{2+}$, $Fe^{2+}$, $Co^{2+}$, $Cu^{2+}$, $Ni^{2+}$, $Zn^{2+}$, or $Ca^{2+}$, $M^{III}$ is a trivalent cation such as $Al^{3+}$, $Cr^{3+}$, $Mn^{3+}$, $Fe^{3+}$, $Co^{3+}$, or $La^{3+}$, and $A^{n-1}$ is the anion, commonly carbonate and hydroxide.

Figure 2:
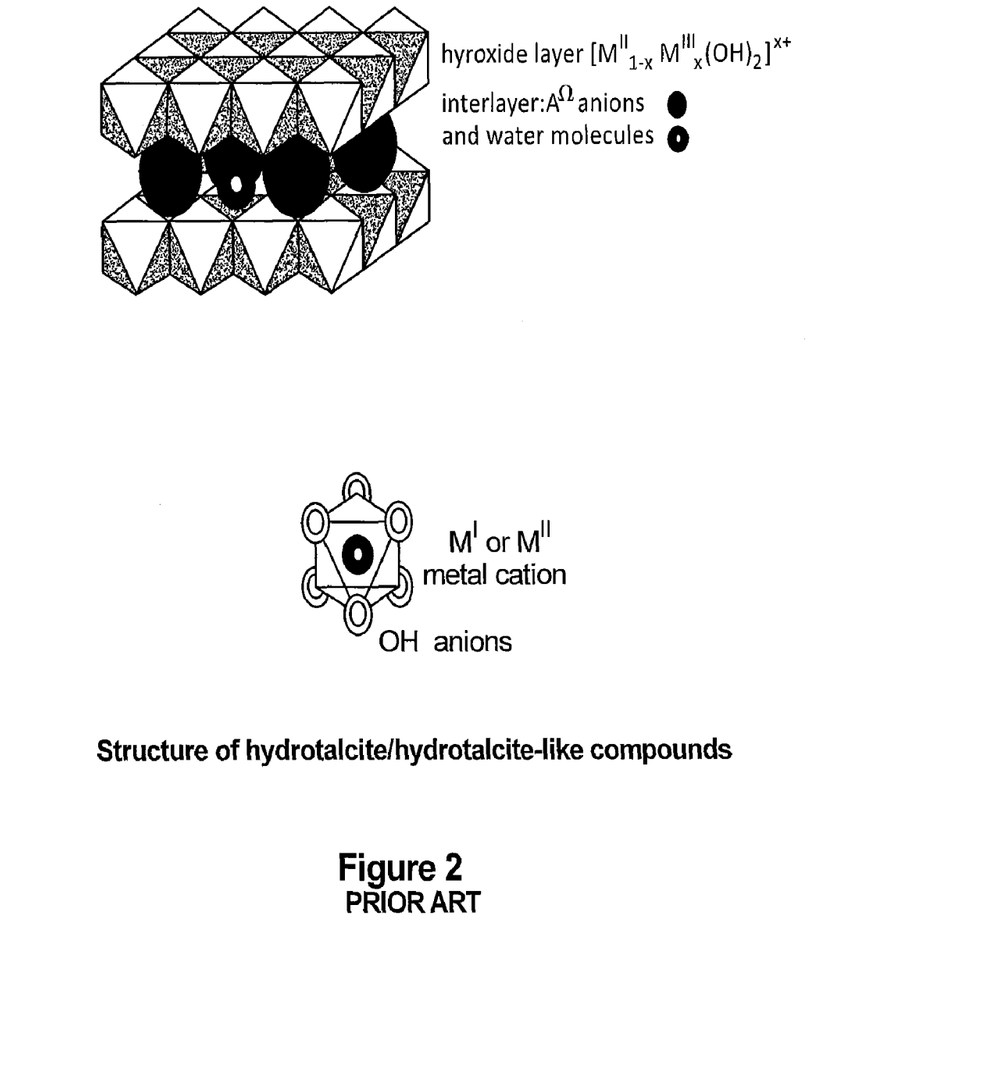
FIG. 2 shows hydrotalcite and hydrotalcite-like compounds have layered structure composed of hydroxide layers $[M^{II}_{1-x}M^{III}_x(OH)_2]^{x+}$.

As illustrated in FIG. 2, hydrotalcite and hydrotalcite-like compounds have a layered structure composed of hydroxide layers $[M^{II}_{1-x}M^{III}_x(OH)_2]^{x+}$, each with multiple positive charges, and interlayers containing anions and water molecules. The preferred $M^{II}$ is $Mg^{2+}$ and the preferred $M^{III}$ is $Al^{3+}$. The value of x represents a portion of trivalent metal cations substituted in the hydroxide layers and usually corresponds to $0.2 < x < 0.35$.

Synthetic hydrotalcite and hydrotalcite-like compounds with a $M^{II}/M^{III}$ molar ratio of 2.0:1 or higher are preferred, though commercial hydrotalcite with the same $M^{II}/M^{III}$ molar ratio can also be used. Since hydrotalcite/hydrotalcite-like compounds may also contain carbonate, which adversely affects their effectiveness as catalysts for the alkoxylation process described in this invention, calcination via heat treatment of hydrotalcite/hydrotalcite-like compounds may be necessary prior to their being used in the preparation of the initiator. It is important to note that the hydrotalcite/hydrotalcite-like compound contains water in its anion interlayers and that its reaction with the intermediate (III), which yields water as by-product, is reversible. Therefore, to maximize the formation of the desired macromolecular initiator, the water by-product must be removed from the reaction mixture of intermediate (III) and hydrotalcite as soon as it is formed.

Also as discovered in this invention, selected organic compounds with amphoteric structure (IV) may also be used as catalysts for the alkoxylation process described in this invention.

(IV)

These organic compounds possess a unique ionic structure with no separate anion and counterion. They include Zwitter ions, betaines, and amine oxides, wherein $R_1$, $R_2$, $R_3$ are alkyl or alkylene oxide groups, $N^+$ is an ammonium group, and $A^-$ is alkoxide, carboxylate, or oxides. Though the simple amphoteric structure consists of one $N^+$ and one $A^-$, other amphoteric materials may have two or more of each of these two groups in each molecule.

Among the three groups of amphoteric compounds, Zwitter ions are the most effective catalysts for the alkoxylation process described in this invention. Zwitter ions such as those having the structures (XI) and (XIII) are prepared from the reaction of their corresponding tertiary amine precursors with ethylene oxide.

(X)   (XI)

-continued

The preferred Zwitter ions of Type (XI) are normally derived from alkyl dimethylamine ($R_1$=alkyl, $R^2/R^3$=methyl), such as tallowalkyl dimethylamine, cocoalkyl dimethylamine, dodecyl dimethylamine, and the like, or ethoxylated alkyl/alkyl ether amine such as ethoxylated tallow amine, ethoxylated coco amine, ethoxylated soya amine, ethoxylated oleyl amine, ethoxylated decyl ether amine, ethoxylated dodecyl ether amine, ethoxylated tridecyl ether amine, ethoxylated tetradecyl ether amine, and the like. The preferred Zwitter ion of Type (XIII) is derived from tetramethylethylene diamine (R4, $R_5$, $R_6$, R7=methyl, n=2) or tetramethylbutylene diamine (R4, $R_5$, $R_6$, R7=methyl; n=4). The Zwitter ions can be prepared separately prior to being used as catalyst for the ethoxylation process, or produced in situ during the initial phase of Stage 2 of the process. Either way, their effectiveness remains the same.

The alkoxylation process utilized in the present invention also includes two stages. In Stage 1 of the present process, the tertiary amine intermediate (III) is prepared via the reaction of one mole of the selected alkyl (or alkyl ether) amine with typically two moles of the alkylene oxide at temperature that varies from 160-190° C. and at pressure that varies from 40-90 psig. Typically, the intermediate (III) is prepared immediately prior to its further alkoxylation. However, for ethoxylated products based on tallow or coco amine, Stage 1 can be by-passed by using the commercially available N,N-bis(2-hydroxyethyl)-N-alkylamine based on cocoamine (Ethomeen C/12 from Akzo Nobel) or based on tallowamine (Ethomeen T/12).

In Stage 2 of the new process using strontium/barium hydroxide or hydrotalcite compound as catalyst, the intermediate (III) is reacted with strontium/barium hydroxide or hydrotalcite compounds at 135-145° C. under nitrogen purging or vacuum for 0.5-1.0 hour, or until the moisture content of the reaction mixture is less than 0.1% to generate the desired initiator that initiates the polymerization of alkylene oxide as soon as it is introduced to the reactor. The concentration of strontium/barium hydroxide or hydrotalcite, the number of moles of alkylene oxide, and the alkoxylation temperature are critical factors. For the preparation of the ethoxylated products, the concentration of strontium/barium hydroxide or hydrotalcite must be in the range of 0.05-0.50 weight percent of the batch weight and preferably in the range of 0.15-0.30 weight percent of the batch weight. The number of the moles of ethylene oxide used in this stage is preferred to be in the range of 1-13, and in another embodiment 2-9. It is possible to use many sub-stages within stages 1 and 2 and end up with the same total EO addition. The ethoxylation temperature must be maintained in the range of 140-200° C., preferably in the range of 160-180° C. Ethoxylation performed at lower than 130° C. is extremely slow, and normally stops before all the ethylene oxide is consumed.

In the Stage 2 of the new process using the Zwitter ion, the intermediate (III) is reacted with the Zwitter ion at 110-120° C. for 0.5 to 1.0 hour to generate the desired initiator that initiates the polymerization of alkylene oxide as soon as it is introduced to the reactor. The concentration of the Zwitter ion, the number of moles of alkylene oxide, and the alkoxylation temperature are critical factors. For the preparation of the ethoxylated products, the concentration of the Zwitter ion must be in the range of 0.50-10.00 weight percent of the batch weight and is preferred to be in the range of 2.0-5.00 weight percent of the batch weight. The number of moles of ethylene oxide used in this stage is preferred to be in the range of 1-10, and in another embodiment 2-8. It is possible to use many sub-stages within stages 1 and 2 and end up with the same total EO addition. The ethoxylation temperature must be maintained in the range of 100-130° C., preferably in the range of 110-120° C. Ethoxylation performed at lower than 100° C. or higher than 130° C. is extremely slow, and normally stops before all the ethylene oxide is consumed.

Since water can undergo the catalyzed reaction with ethylene oxide to yield undesired by-products, it is important that the two ethoxylation stages are performed under the anhydrous condition. To attain this condition, drying of the material (alkylamine or alkyl ether amine) and the ethoxylation equipment is done before Stage 1 by heating the material and the equipment to a temperature of 100-150° C. under nitrogen purging or vacuum, until the content of the water in the material is less than 0.1 percent, and preferably less than 0.05 percent, of its weight. When strontium/barium hydroxide or hydrotalcite is used as the catalyst, drying is also done under the same conditions after the catalyst is blended with the intermediate (III) resulting from Stage 1.

The preferred starting alkylamines include, but are not limited to, those derived from tallow, coconut oil, soybean oil, palm kernel oil, and mixtures thereof. The preferred starting ether amines include, but are not limited to, decyl ether amine, undecyl ether amine, dodecyl ether amine, tridecyl ether amine, tetradecyl ether amine, hexadecyl ether amine, octadecyl ether amine, and mixtures thereof. In a preferred embodiment, the starting amines are of the formula:

$$R—NH_2$$

wherein R is selected from a linear or branched, saturated or non-saturated alkyl group containing 8-22 carbon atoms; in another embodiment, 12-22 carbon atoms; in yet another embodiment, 16-22 carbon atoms.

To compare alkylene oxide distribution in an alkoxylated alkylamine, use of degree of peaking is helpful. The degree of peaking is defined as the sum of the areas for the adjacent three most abundant peaks.

The relative degrees of peaking of ethoxylates prepared according to the process of the present invention were measured and compared to their counterparts prepared via conventional ethoxylation using sodium/potassium hydroxide as the initiator precursor.

For degree of peaking determinations, area percent determined by gas chromatography (GC) was used. The degree of peaking is expressed as a weight percentage (%). The higher the weight percentage, the narrower the molecular weight distribution. The formula and method for determination of the molecular weight distribution can be found in "Narrow Alcohol Ethoxylates," *Annual Surfactants Reviews*, Vol. 2, Ed. D. R. Karsa (1999) and, with some modification, can be adapted for alkoxylated alkylamines.

The alkoxylated alkylamines having the peaked distribution of the present invention are characterized in having a peaked distribution defined by a degree of peaking of at least 5% greater than the distribution of a conventional alkoxylated amine composition prepared via conventional base catalysis. In another embodiment, the degree of peaking is at least 6% greater, preferably 7% greater than the distribution of a conventional alkoxylated amine composition prepared via conventional base catalysis. In still another embodiment, the degree of peaking is at least 10% greater than the distribution of a conventional alkoxylated amine composition prepared via conventional base catalysis.

The preferred alkoxylated alkylamines with peaked distribution include, but are not limited to, ethoxylated tallow amine with 3 to 15 EO, ethoxylated coco amine with 3 to 15 EO, and mixtures thereof. Preferred alkoxylated alkyl ether amines with peaked distribution include, but are not limited to, ethoxylated dodecyl ether amine with 3 to 15 EO, ethoxylated tridecyl ether amine with 3 to 15 EO, ethoxylated tetradecyl ether amine with 3 to 15 EO, ethoxylated hexadecyl ether amine with 4 to 15 EO, ethoxylated octadecyl ether amine with 3 to 15 EO, and mixtures thereof.

Though not required, a solvent that is inert toward the reaction with ethylene oxide can also be used to improve the handling of the starting alkylamine or the resulting ethoxylated product, or to meet the minimum initial volume of material for proper mixing action with ethylene oxide as required for each ethoxylation reactor. Aromatic solvents, such as xylene, toluene, alkyl benzenes such as ethyl benzene, hexyl benzene, dodecyl benzene, alkyl naphthalenes such as methyl and dimethyl naphthalene, isopropyl and di-isopropyl naphthalene, or commercial aromatic solvents, such as Aromatic Solvent 100, 150 or 200 available from ExxonMobil, or organic ethers such as dibutyl ether, and the like are suitable solvents for the process of this invention.

The invention will now be illustrated by the following non-limiting examples.

Example 1

Preparation of Ethoxylated Tallow Amine Using 5 Moles of Ethylene Oxide with Barium Hydroxide as Catalyst Stage 1: Distilled tallow amine (680 g, 2.6 moles) was charged to a one-gallon stainless steel pressure vessel and then heated at 150° C. under nitrogen purging for 30 minutes to reduce its moisture content to less than 0.1%. Ethylene oxide (230 g, 5.23 moles) was then added to the pressure vessel over a period of 40 minutes while the temperature was maintained at 150-160° C. Following a 30-minute period of digestion, the reaction mixture was cooled to 110° C., sampled, and analyzed. Its Total Amine Value was 2.86 me/g, indicating that 2.00 moles of ethylene oxide had been consumed for the ethoxylation of 1 mole of tallow amine.

Stage 2: Barium hydroxide (3 g) was charged to the pressure vessel. The reaction mixture was purged with nitrogen, then heated at 135° C. for 30 minutes under nitrogen purging to reduce its moisture content to less than 0.1%. The reaction mixture was then heated to 150° C. Ethylene oxide (345 g, 7.84 moles) was then added to the pressure vessel over a period of 20 minutes while the temperature was maintained at 160-170° C. Following a 30-minute period of digestion, the reaction mixture was purged with nitrogen to remove the trace of unreacted ethylene oxide, then cooled to 50° C., and discharged. Its TAV was 2.08 me/g, indicating that a total of 5.0 moles of ethylene oxide had been consumed for the ethoxylation of each mole of tallow amine. The contents of dioxane (about 150 ppm) and EGDs (about 2.5%) of the final product are much lower than the contents of dioxane (about 5,000 ppm) and EGDs (about 6.5%) of its counterpart made by the acid-catalyzed process.

Figure 3:
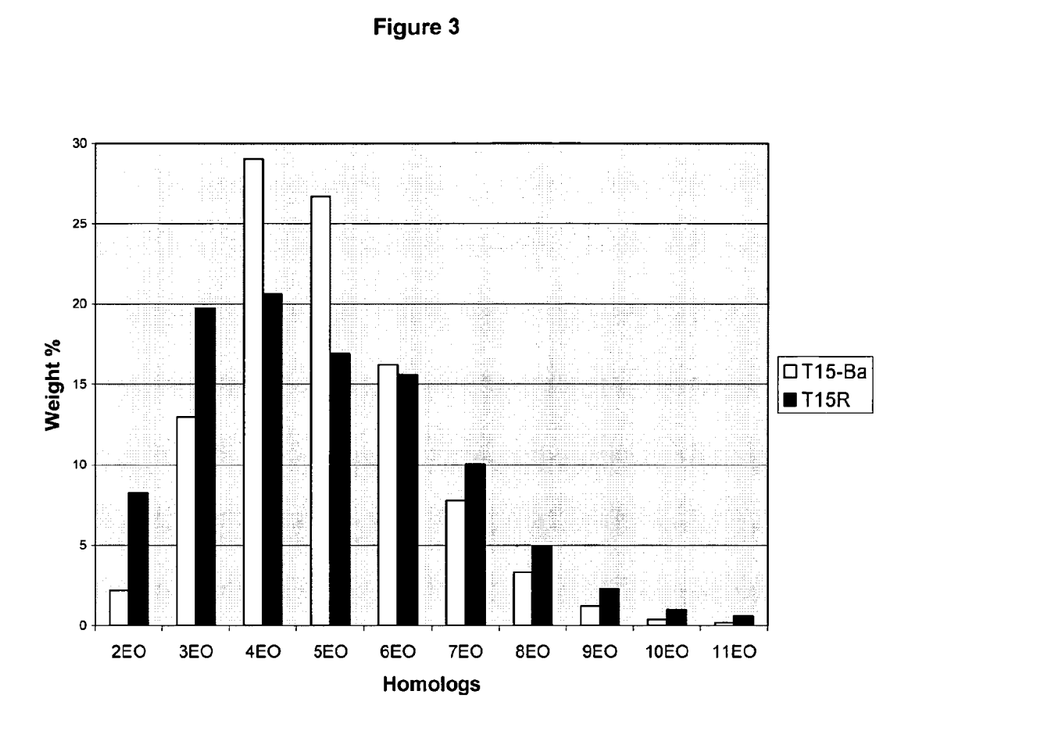
FIG. 3 shows the homolog distribution of the 5-mole EO adduct of coco amine prepared by the regular ethoxylation process (T15R) and the new ethoxylation process (T15-Ba). The degree of peaking is 57.3 for T15R and 71.9 for T15-Ba

FIG. 3 illustrates the homologs distribution of the resulting ethoxylated product (T15-Ba) and of its counterpart prepared by regular ethoxylation, with potassium hydroxide as the initiator precursor, of the tallow amine with the same number of moles (5) of ethylene oxide with the same Total Amine Value (TI 5R). The degree of peaking is 71.9 for T15-Ba and 57.3 for T15R, indicating that the T15-Ba product made by the new process possesses a peaked ethoxylation distribution.

Example 2

Preparation of Ethoxylated Tallow Amine Using 10 Moles of Ethylene Oxide with Strontium Hydroxide as Catalyst Stage 1: Distilled tallow amine (680 g, 2.6 moles) was charged to a one-gallon stainless steel pressure vessel and then heated at 150° C. under nitrogen purging for 30 minutes to reduce its moisture content to less than 0.1%. Ethylene oxide (230 g, 5.23 moles) was then added to the pressure vessel over a period of 40 minutes while the temperature was maintained at 150-160° C. Following a 30-minute period of digestion, the reaction mixture was cooled to 110° C., sampled, and analyzed. Its Total Amine Value was 2.86 me/g, indicating that 2.00 moles of ethylene oxide had been consumed for the ethoxylation of 1 mole of coco amine.

Stage 2: Strontium hydroxide (3 g) was charged to the pressure vessel. The reaction mixture was purged with nitrogen, then heated at 135° C. for 30 minutes under nitrogen purging to reduce its moisture content to less than 0.1%. The reaction mixture was then heated to 150° C. Ethylene oxide (570 g, 12.95 moles) was then added to the pressure vessel over a period of 20 minutes while the temperature was maintained at 160-170° C. Following a 30-minute period of digestion, the reaction mixture was purged with nitrogen to remove the trace of unreacted ethylene oxide, then cooled to 50° C., and discharged. Its TAV was 1.44 me/g, indicating that a total of 9.9 moles of ethylene oxide had been consumed for the ethoxylation of each mole of tallow amine. The contents of dioxane (about 150 ppm) and EGDs (about 3.5%) of the final product are much lower than the contents of dioxane (about 9,000 ppm) and EGDs (about 11.5%) of its counterpart made by the acid-catalyzed process.

Figure 4:
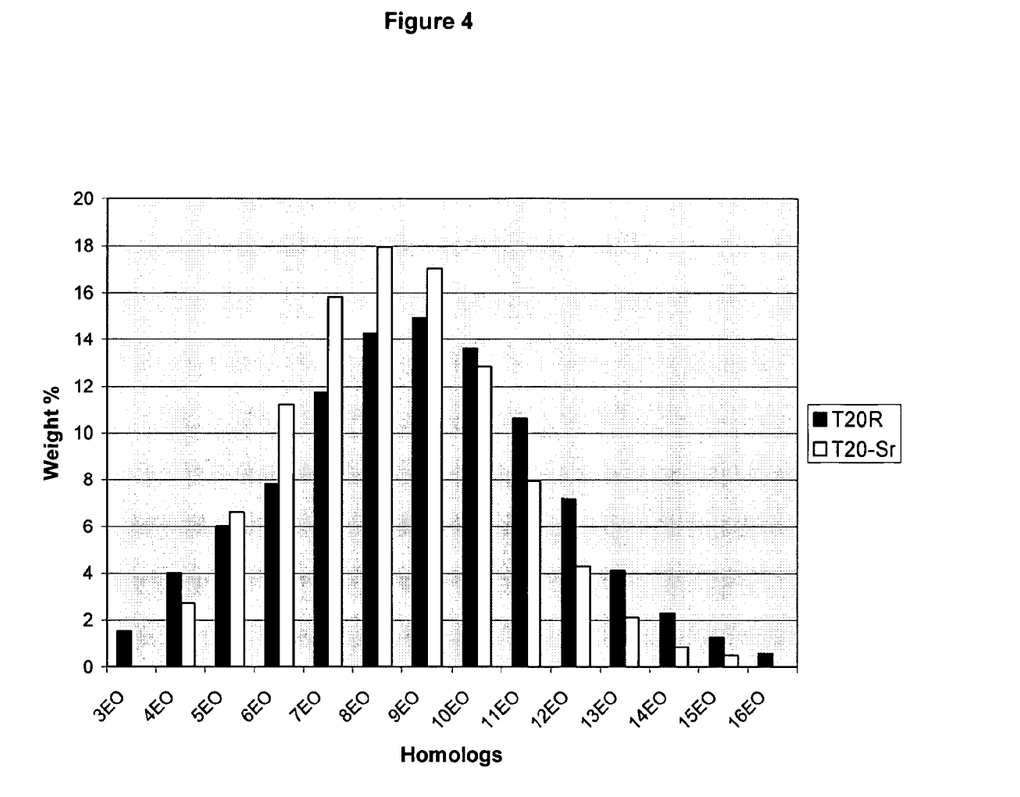
FIG. 4 shows the Homolog distribution of 10-mole EO adduct of coco amine prepared by the regular ethoxylation process (T20R) and the new ethoxylation process (T20-Sr). The degree of peaking is 42.8 for T20R and 50.8 for T20-Sr.

FIG. 4 illustrates the homologs distribution of the resulting ethoxylated product (T20-Sr) and of its counterpart prepared by regular ethoxylation using potassium hydroxide as initiator precursor of the tallow amine with the same number of moles (10) of ethylene oxide (T20R). The degree of peaking is 50.8 for T20-Sr and 42.8 for T20R, indicating that the T20-Sr product made by the new process possesses a peaked ethoxylation distribution.

Example 3

Preparation of Ethoxylated Tallow Amine Using 5 Moles of Ethylene Oxide with Hydrotalcite as Catalyst

In this experiment, the Stage 1 ethoxylation (non-catalyzed reaction of coco amine with 2 moles of ethylene oxide) was by-passed. Instead, the commercially available Ethomeen T/12, having a Total Amine Value of 2.88 me/g, was used as the starting material. Commercial hydrotalcite was obtained from Aldrich Chemicals. Prior to its use as the initiator precursor, the commercial hydrotalcite was heated at 400° C. for 30 minutes to remove the carbonate ion in its interlayers. The heat-treated material was then mixed with water to regenerate the anion (hydroxide) and water in the interlayers, and filtered.

Stage 2: Ethomeen T/12 (700 g, 2.02 moles) and treated hydrotalcite (3 g as active) were charged to a one-gallon stainless steel pressure vessel, purged with nitrogen, then heated at 135° C. for 60 minutes to reduce the moisture content to less than 0.1%. The mixture was heated to 160° C. Ethylene oxide (270 g, 6.14 moles) was then added to the pressure vessel over a period of 75 minutes, while the temperature was maintained at 160-175° C. Following a 60-minute period of digestion, the reaction mixture was purged with nitrogen, cooled to 50° C., then discharged and analyzed. Its Total Amine Value was 2.10/g, indicating that in this stage, 2.86 moles of ethylene oxide had been consumed for the ethoxylation of 1 mole of Ethomeen T/12. The contents of dioxane (about 400 ppm) and EGDs (about 2.7%) of the final product are much lower than the contents of dioxane (about 5000 ppm) and EGDs (about 7.5%) of its counterpart made by the acid-catalyzed process.

Figure 5:
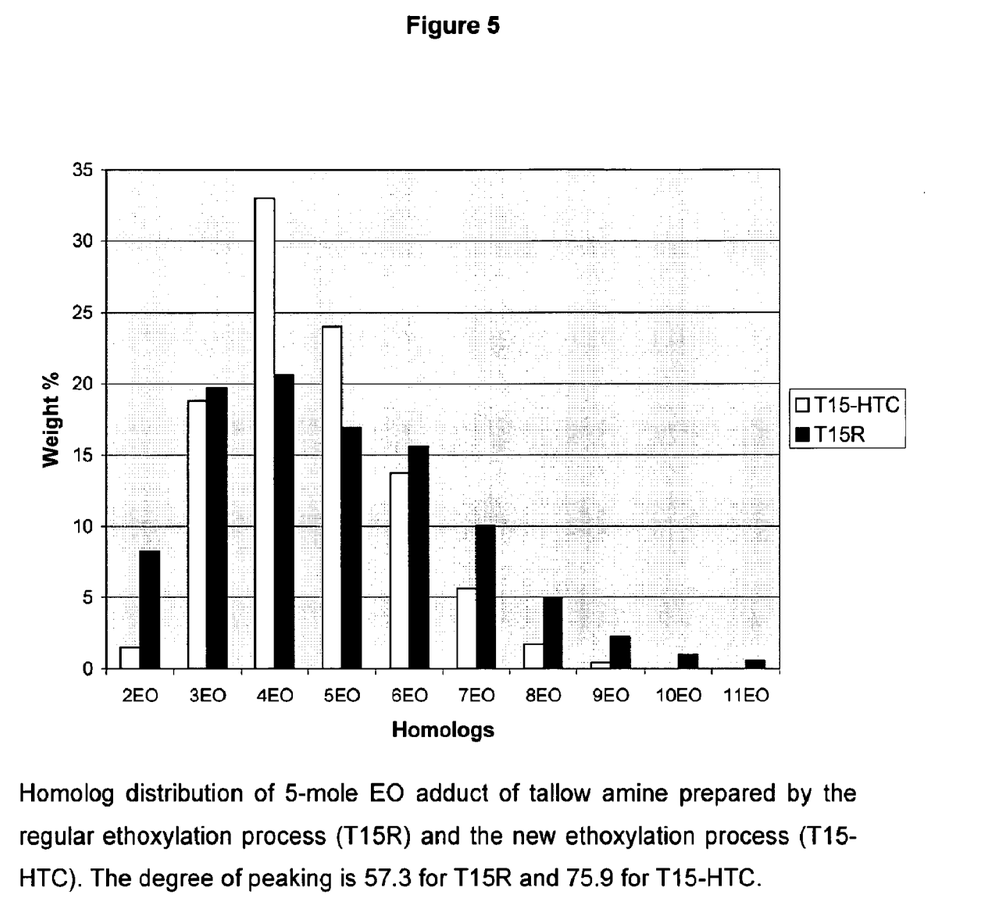
FIG. 5 shows homolog distribution of 5-mole EO adduct of tallow amine prepare by regular ethoxylation process (T15R) and new ethoxylation process (T15-HTC).The degree of peaking is 57.3 for T15R and 75.9 for T15-HTC.

FIG. 5 illustrates the homologs distribution of the resulting ethoxylated product (T15-HTC) and of its counterpart prepared by regular ethoxylation using potassium hydroxide as initiator precursor of the tallow amine with the same number of moles (5) of the ethylene oxide (T15R). The degree of peaking is 75.9 for T15-HTC and 57.3 for T15R, indicating that the T15-HTC product made by the new process possesses a peaked ethoxylation distribution.

The invention claimed is:

1. A process for preparing alkoxylated alkyl (ether) amines of formula (I) with peaked distribution using a catalyst with a multiple-charge counterion, wherein said process comprises reacting, in a first step, a primary alkylamine (II) with an alkylene oxide in order to yield the first intermediate (III)

followed by reacting, in a second step, the intermediate (III) with (m) additional moles of alkylene oxide in the presence of a catalyst with multiple-charge counterions to yield the desired final alkoxylated alkyl (ether) amine product (I)

wherein R is selected from a linear or branched, saturated or non-saturated alkyl group containing 8-22 carbon atoms, or is a group of the formula:

wherein A, B, X, Y, are alkylene oxide groups containing 2-4 carbon atoms, C is an alkylene group containing 3-4 carbon atoms, a, b each vary from 0-5, c is 1, x is 1, y varies from 1-15, n moles of alkylene oxide is from 1 to 2, and m moles of alkylene oxide is from 1-18.

2. The process of claim 1 wherein step 1 is uncatalyzed, and step 2 is initiated with a catalyst with a multiple-charge counterion.

3. The process of claim 2 wherein the catalyst with the multiple-charge counterion is a binary compound of Group II elements.

4. The process of claim 2 wherein the catalyst with the multiple-charge counterion is hydrotalcite or a hydrotalcite-like compound having a hydroxide layer, of the general formula $M^{II}_{1-x}M^{III}_{x}(OH)_2 A^{n-1}_{x/n} \cdot mH_2O$, wherein $M^{II}$ is a divalent cation, $M^{III}$ is a trivalent cation, and $A^{n-1}$ is the anion, wherein n is an integer greater than 1 and x represents the portion of the trivalent metal cations substituted in the hydroxide layer.

5. The process of claim 2 wherein the catalyst with the multiple-charge counterion is a Zwitter ion having the structure (XI), (XIII), (XV)

or mixtures or combinations thereof, wherein R1 to R11 are each independently selected from saturated or unsaturated, linear or branched alkyl groups having from 8 to 22 carbon atoms, n is 2 or 4, and whereby the ethoxylation temperature is in the range of 100-130° C., and the amount of zwitter ion catalyst is 0.5-10.0% by weight of the batch weight.

6. The process of claim 3 wherein the binary compounds of Group II elements are strontium hydroxide, barium hydroxide, strontium acetate, barium acetate, or mixtures thereof.

7. The process of claim 4 wherein the catalyst with the multiple charge is hydrotalcite or hydrotalcite-like compounds having a hydroxide layer wherein $M^{II}$ is $Mg^{2+}$, $Fe^{2+}$, $Co^{2+}$, $Cu^{2+}$, $Ni^{2+}$, $Zn^{2+}$, or $Ca^{2+}$, and $M^{III}$ is $Al^{3+}$, $Cr^{3+}$, $Mn^{3+}$, $Fe^{3+}$, $Co^{3+}$, or $La^{3+}$ wherein x represents the portion of the trivalent metal cations substituted in the hydroxide layer.

8. The process of claim 4 wherein $M^{II}$ is magnesium and $M^{III}$ is aluminium, and with a magnesium-aluminium molar ratio of 2.0:1.0 or greater.

9. The process of claim 2 wherein the catalyst with the multiple-charge counterion is a mixture of hydrotalcite with a magnesium-aluminium molar ratio of 2.0:1.0 or greater, and strontium hydroxide or barium hydroxide.

10. The process of claim 5 wherein the Zwitter ion of structure (XI) is prepared by reacting alkyl dimethylamine with one mole of alkylene oxide.

11. The process of claim 5 wherein the Zwitter ion of structure (XI) is prepared by reacting the intermediate (III) with one mole of alkylene oxide.

12. The process of claim 5 wherein the Zwitter ion (XI) is prepared by reacting bis-(2-hydroxyethyl)-N-alkylamine with alkylene oxide.

13. The process of claim 5 wherein the Zwitter ion (XIII) is prepared by reacting tetraalkylalkylene diamine with 2 moles of alkylene oxide.

14. The process of claim 13 wherein the tetraalkylalkylene diamine is tetramethylbutylene diamine, tetramethylethylene diamine, and tetramethyl-hexylene diamine.

15. The process of claim 5 wherein the Zwitter ion (XIII) is prepared by reacting dialkylalkylene diamine with alkylene oxide.

16. The process of claim 5 wherein the Zwitter ion of structure (XV) is prepared by reacting polyalkylpolyethylene polyamine containing x amino groups in each molecule with one to x moles of alkylene oxide.

17. The process of claim 5 wherein the Zwitter ion of structure (XV) is prepared by reacting the poly[(2-hydroxyethyl)]polyethylene polyamine containing x amino groups in each molecule with one to x moles of alkylene oxide.

18. The process of claim 15 wherein dialkylalkylene diamine is selected from dimethylethylene diamine, dimethylbutylene diamine, dimethylhexalene diamine, and dimethyl aminopropylamine.

19. The process of claim 17 wherein poly[(2-hydroxyethyl)]polyethylene polyamine is prepared by the reaction of alkylene oxide with a polyethylene polyamine selected from ethylene diamine, diethylene triamine, and tetraethylene pentamine.

20. The process of claim 1 wherein the (m) additional moles of alkylene oxide are controlled at from 2-18.

21. In a process for the preparation of alkoxylated alkylamines of formula (I) through the use of conventional base catalysts, the improvement comprising preparing said amines using a catalyst with a multiple-charge counterion in accordance with the process of claim 1 in order to obtain amines of formula (I) with peaked distribution have a degree of peaking at least 5% greater than the distribution of a conventional alkoxylated amine composition prepared via conventional base catalysis.

22. The process of claim1 wherein the alkoxylated alkylamine of formula (I) is selected from ethoxylated tallow amine with 5 to 15 EO, ethoxylated soya amine with 5-15 EO, ethoxylated coco amine with 5 to 15 EO, and mixtures thereof.

23. The process of claim 1 wherein the alkoxylated alkylamine is an ethoxylated alkyl ether amine selected from the group consisting essentially of ethoxylated decyl ether amine with 3 to 15 EO, ethoxylated dodecyl ether amine with 3 to 15 EO, ethoxylated tridecyl ether amine with 3 to 15 EO, ethoxylated tetradecyl ether amine with 3 to 15 EO, ethoxylated hexadecyl ether amine with 3 to 15 EO, ethoxylated octadecyl ether amine with 3 to 15 EO, and mixtures thereof.

24. A process for the ethoxylation of an alkyl amine in order to obtain a peaked distribution product, wherein the starting alkyl amine is selected from the group consisting essentially of a dialkyl amine, an alkyl diamine, an alkyl ether amine, or an alkyl ether diamine, said process comprising:

in a first step, reacting the starting alkyl amine with 2 moles of ethylene oxide at a temperature of from 160 -190° C. to yield the tertiary intermediate, and in a second step further reacting the tertiary amine intermediate with (v) additional moles of ethylene oxide in order to obtain a final product wherein said second step is conducted in the presence of a catalyst with multiple counter ions.

25. The process of claim 24 wherein the starting alkylamine is a dialkylamine, an alkyl diamine, or mixtures thereof derived from tallow, coconut, soybean, palm, and palm kernel oils and mixtures thereof.

26. The process of claim 24 wherein the starting alkylamine is a (di)alkyl ether amine, or an alkyl ether diamine selected from the group consisting of decyl ether amine, dodecyl ether amine, tridecyl ether amine, tetradecyl ether amine, hexadecyl ether amine, octadecyl ether amine, decyl ether diamine, dodecyl ether amine, tridecyl ether diamine, tetradecyl ether diamine, hexadecyl ether diamine, octadecyl ether diamine, and mixtures thereof.

27. A process according to claim 1 for the ethoxylation of primary alkylamine (VI) in order to obtain a peaked distribution product which comprises:

in a first step, reacting the starting primary alkylamine (VI) with 2 moles of ethylene oxide at a temperature of from 160-190° C. to yield the tertiary intermediate (VII) (N,N-bis-(2-hydroxyethyl) N-alkylamine)

in a second step, further reacting the tertiary amine intermediate (VII) with (v) additional moles of ethylene oxide in order to obtain a final product (VIII)

wherein said second step is conducted in the presence of a catalyst with multiple counterions selected from strontium hydroxide, barium hydroxide, strontium acetate, barium acetate, hydrotalcite, or with a Zwitter ion formed from the reaction of trialkylamine, alkyl dimethylamine, alkylamine, tetramethylbutylene diamine, tetramethylethylene diamine, ethoxylated alkylamine, ethoxylated alkyl diamine, or a mixture thereof with ethylene oxide.

* * * * *